United States Patent [19]

van Wiltenburg

[11] Patent Number: 5,149,530
[45] Date of Patent: Sep. 22, 1992

[54] LIVE NEWCASTLE DISEASE VIRUS VACCINES

[75] Inventor: Nico van Wiltenburg, Weesp, Netherlands

[73] Assignee: Duphar International Research B.V., Weesp, Netherlands

[21] Appl. No.: 379,232

[22] Filed: Jul. 13, 1989

[30] Foreign Application Priority Data

Jul. 18, 1988 [NL] Netherlands .................... 8801819

[51] Int. Cl.$^5$ .................... A61K 39/12; C12N 7/00
[52] U.S. Cl. .................... 424/89; 435/235.1; 435/236; 435/237; 435/239; 435/948
[58] Field of Search ............ 424/89; 435/235.1, 236, 435/237, 239, 948

[56] References Cited

U.S. PATENT DOCUMENTS

| | | | |
|---|---|---|---|
| 2,798,835 | 7/1957 | Markham et al. | 424/89 |
| 3,876,763 | 4/1975 | Yoshiazu et al. | 424/89 |
| 4,053,583 | 10/1977 | Gits et al. | 424/89 |
| 4,235,876 | 11/1980 | Gits et al. | 424/89 |
| 4,279,893 | 7/1981 | Kreimer et al. | 424/89 |
| 4,537,768 | 8/1985 | Apontoweil et al. | 424/89 |

OTHER PUBLICATIONS

Hanson et al., *Am. Journal of Veterinary Research*, vol. 17, pp. 294–298, Apr. 1956.
C. W. Beard, *Avian Diseases*, vol. 11, pp. 399–406, 1967.
Winterfield et al., *Am. Journal of Veterinary Research*, vol. 36, no. 4 pp. 524–526, 1965.
Winterfield, *Avian Diseases*, vol. 12, p. 577, 1968.
Borlanud et al., *Biological Abstract*, vol. 71(1). Ref. # 2874, 1980.
Borland et al., *Avian Pathology*, vol. 9, pp. 261–269, 1980.
Borland, L. J. and Allan, W. H., "Development of Newcastle Disease Vaccine (2) Stability Testing of Clone-Purified Virus" Avian Pathology, 9: 271–275, 1980.
Borland, L. J. and Allan W. H., "Laboratory Tests for Comparing Live Lentogenic Newcastle Disease Vaccines" Avian Pathology, 9: 45–49, 1980.

*Primary Examiner*—Johnnie R. Brown
*Assistant Examiner*—Abdel A. Mohamed
*Attorney, Agent, or Firm*—Stevens, Davis, Miller & Mosher

[57] ABSTRACT

The invention relates to a live virus vaccine against Newcastle Disease containing at least $^{10}$log 5.5 EID$_{50}$ per dose of the strain NDW, deposited at the CNCM of Institut Pasteur in Paris under accession no. I-781.

5 Claims, No Drawings

LIVE NEWCASTLE DISEASE VIRUS VACCINES

The invention relates to live Newcastle Disease virus (NDV)vaccines for poultry, to a method of preparing the same and to a new NDV-strain.

ND is a disorder of the respiratory tract, the laying system, the intestines and the central nervous system, frequently occurring in poultry.

The disease causes great economical losses in poultry farming. In addition to mortality of animals, the disease causes respiratory and nervous symptoms, and in layers decrease of production as result of damage to the laying system.

The disease is controlled by vaccinating the animals with a live or an inactivated vaccine. For example, vaccinations with live vaccines based on among others the Hitchner-strain or the De la Sota-strain have been carried out for a considerable period of time already. Although the use of vaccines based on the said known NDV strains is comparatively safe and effective, it has been found that in the vaccination of young chickens a strong vaccination reaction nevertheless occurs when the vaccination is done with a strain which provides a good protection. On the other hand the protection is not complete when vaccination is carried out with a strain which causes little vaccination reaction. In this connection the material immunity plays an important role since, for causing the vaccination in chickens with a maternal immunity to be effective, vaccination strains are required which causes a considerable vaccination reaction.

Another disadvantage of the NDV-vaccines based on the known strains is that vaccination with combination vaccines against ND and infectious bronchitis (IB) is not possible due to the occurrence of unacceptably strong vaccination reactions.

It has now been found surprisingly that ND vaccines which do not have the disadvantage mentioned hereinbefore are obtained when the NDV strain used is the strain Newcastle Disease virus "Wiltenberg" (NDW) which is registered at the CNCM of the Institut Pasteur, in Paris, under accession number I-781, the said strain having been deposited (under date of Jul. 12, 1988), in accordance with the "Budapest Treaty on the International Recognition of the Deposit of Microorganisms for the Purpose of Patent Procedures, " with the Collection Nationale de Cultures de Microorganimes, CNCM, Institut Pasteur, 25 Rue du Docteur Roux, 75724 Paris Cedex 15.

It has been found that live vaccines based on the strain NDW are completely safe and readily efficacious, also for the protection of chickens having a high maternal immunity. Therefore, vaccine according to the invention may be used already at an age of 1 day.

It has furthermore been found that a generally known problem which occurs when vaccines are administered which contain more than one live virus component, namely the fact that the combined viruses become less immunogenic due to a mutual interaction (so-called interference, see Am. J. Vet. Res. 36 (1965), p. 4, 524 and 525; and Avian Diseases 12 (1968), p. 577) does not occur when the NDW-strain is combined with other live virus strains.

The NDW virus strain can be processed in a manner known per se to a vaccine suitable for administration. Such a vaccine may be administered to chickens from the age of 1 day or at a later date, even when they have a high maternal immunity, if desired in combination with one or more IB-virus strains. The administration may be carried out, for example, by means of a spray or eyedrops.

The invention will now be described in greater detail with reference to the ensuing experiments.

EXPERIMENT I

Efficacy of vaccination with strain NDW

24 Birds taken from a group of 1-day-old broilers were used for the determination of the maternal immunity according to the HI-method. The mean titer was found to be $^2$log 10.7.

43 chickens were vaccinated with $^{10}$log 5.4 EID$_{50}$ per bird by means of spray vaccination. 3 and 6 weeks after vaccination 21 and 22 birds, respectively, were subjected to a challenge infection with $^{10}$log 6 ELD$_{50}$ of Herts 33 virus, administered ocularly, per bird. As a control, at the time of challenge, 2 SPF chickens, 1 week older than the broilers, were added and also challenged.

After the challenge at 3 weeks post vaccination, all 21 birds survived, while after the challenge at 6 weeks post vaccination 20 out of 22 birds survived. The SPF controls died.

It appears from this experiment that the vaccination with the strain NDW of chickens having a high maternal immunity provides excellent protection against an infection with virulent ND virus throughout the fattening period.

EXPERIMENT II

Efficacy of vaccination with the NDW-strain as a component of an ND/IB combination vaccine 48 broilers having a mean maternal antibody titer of $^2$log 10.7 HI units were vaccinated by means of spray at the age of 1 day with a combination vaccine consisting of $^{10}$log 5.4 EID$_{50}$ NDW and $^{10}$log 4.0 EID$_{50}$ H120/84-3 per dose.

3 and 6 weeks post vaccination 23 and 25 birds, respectively, were subjected to an ocular challenge with $^{10}$log 6.5 ELD$_{50}$ of Herts 33 virus per bird. As a control, at the time of challenge, 2 SPF chickens were added and also challenged.

After the challenge at 3 weeks post vaccination, 21 out of the 23 animals survived. After the challenge at 6 weeks post vaccination all 25 birds survived. The SPF controls died.

It appears from this experiment that the NDW-strain administered as a component of an ND/IB combination vaccine provides an excellent protection against infection with virulent ND virus throughout the fattening period. This in spite of the high maternal antibody titre of the chickens at the time of vaccination.

EXPERIMENT III

Efficacy of vaccination with the NDW-strain as a component of an ND/IB combination vaccine 25 birds were taken from a group of 75 day-old broilers for the determination of the maternal antibody titer according to the HI-method. The mean titer was found to be $^2$log 8.7. The remaining chickens were divided into two groups of 25. The first group was vaccinated with a combination vaccine NDW/H120/84-3 in a manner identical to that of experiment 2. The second group formed the non-vaccinated control group. One bird from this group died in the period before challenge. Both groups were infected 32 days post vaccination with $^{10}$log 6.5 ELD$_{50}$ of Herts 33 virus per bird. Two SPF chickens of approximately 6 weeks old were added and also challenged.

1 out of the 25 vaccinated birds died after challenge. 21 out of the 24 non-vaccinated controls died. The SPF controls died.

It appears from this experiment that the NDW strain as a component of an ND/IB combination vaccine provides an excellent protection against infection with virulent ND virus, which confirms the conclusion of experiment 2.

EXPERIMENT 4

Small field trial 1-day-old broilers were distributed over a number of pens and vaccinated with Poulvac IB Primer (IB-strain H120/84-3) or with a combination vaccine consisting of Poulvac IB Primer and NDW vaccine. A few pens were not vaccinated serving as a control group. Each pen housed 400 chickens.

The trachea lesion score, determined at 10 days post vaccination, was 0.0 for the non-vaccinated bird 0.1- 0.6- 0.7- 1.1 for the birds vaccinated with IB Primer (4 groups of 10 birds each)

0.0- 0.0- 0.2- 0.8 for the birds vaccinated with IB Primer/NDW combination (4 groups of 10 birds each)

The mean ND HI titer, determined at 0, 3 and 6 weeks post vaccination was 8.2 (maternal immunity) 4.0 and 4.0, respectively, for birds vaccinated with IB Primer, 8.2, 5.2 and 6.4, respectively, for the birds vaccinated with IB Primer/NDW combination, The average weights, determined at 6 weeks after vaccination, showed no significant differences between the groups.

A challenge with virulent ND virus, strain Herts 33/56, carried out at 4, 5 and 6 weeks post vaccination, resulted in a protection of 90%, 100% and 92%, respectively, in the group vaccinated with IB Primer/NDW combination vaccine. The group vaccinated with IB Primer, as well as the non-vaccinated group, were entirely unprotected against an infection with virulent ND (0% protection) at all three occasions.

A challenge with virulent IB virus, carried out 4 weeks post vaccination, both with the strain Voet and with a virulent strain D274, resulted in a protection of 100% against Voet and 80-100% against D274 for the birds vaccinated with IB Primer a protection of 100% against Voet and 60-100% against D274 for the birds vaccinated with IB Primer/NDW combination no protection (both strains 0% protection) for the non-vaccinated birds.

From this experiment if appears that the NDW strain as a component of an IB/ND combination vaccine is fully harmless provides an excellent protection against infection with virulent ND virus does not interfere with the remaining components of the vaccine, so that these also remain fully efficacious.

I claim:

1. A live vaccine against Newcastle Disease, comprising a virus of the strain NDW (Newcastle Disease virus "Wiltenberg"), registered at the CNCM (Collection Nationale de Cultures de Microorganismes) of the Institut Pasteur in Paris, under accession number I-781, with a pharmaceutically acceptable carrier.

2. A vaccine as claimed in claim 1, comprising an effective quantity of virus $> ^{10}$log 5.5 EID$_{50}$ dose.

3. A vaccine as claimed in claim 1 or 2, further comprising at least one infectious bronchitis virus strain.

4. A method of preventing Newcastle Disease in poultry, comprising vaccinating young chickens, from the first day of life, with at least one vaccine as claimed in claim 1 or 2.

5. Virus strain NDW (Newcastle Disease virus "Wiltenberg"), registered at the CNCM (Collection Nationale de Cultures de Microorganismes) of the Institut Pasteur in Paris under accession number I-781.

* * * * *